United States Patent [19]

Johnston

[11] 4,442,096
[45] Apr. 10, 1984

[54] 2-(SUBSTITUTED)AMINO-3-CYANO-5-HALO-6-(SUBSTITUTED)-PYRAZINE ANTIMICROBIAL COMPOUNDS, COMPOSITIONS AND USE

[75] Inventor: David B. R. Johnston, Warren, N.J.

[73] Assignee: Merck & Co., Inc., Rahway, N.J.

[21] Appl. No.: 453,057

[22] Filed: Dec. 27, 1982

[51] Int. Cl.$^3$ .................... A01N 43/60; A01N 43/84; C07D 241/20; C07D 413/04
[52] U.S. Cl. ..................... 424/248.5; 424/248.52; 424/248.53; 424/248.54; 424/248.55; 424/248.56; 424/250; 544/82; 544/120; 544/121; 544/357; 544/407; 544/408; 544/409; 106/15.05; 106/18.32; 106/18.33; 71/77; 71/88; 71/92
[58] Field of Search .............. 544/82, 120, 121, 357, 544/405, 407, 408, 409; 424/248.5, 248.51, 248.52, 248.53, 248.54, 248.55, 248.56, 250

[56] References Cited

U.S. PATENT DOCUMENTS

| | | |
|---|---|---|
| 3,274,192 | 9/1966 | Cragoe et al. ............... 544/409 |
| 3,299,063 | 1/1967 | Cragoe et al. ............... 544/409 |
| 3,341,540 | 9/1967 | Cragoe et al. ............... 544/409 |
| 3,487,082 | 12/1967 | Cragoe et al. ............... 544/409 |
| 3,626,060 | 12/1971 | Grier ........................... 424/232 |
| 3,763,176 | 10/1973 | Kohn et al. .................. 71/67 |
| 3,854,000 | 12/1974 | Grier et al. .................. 424/270 |
| 4,054,655 | 10/1977 | Donald ........................ 544/409 |
| 4,119,779 | 10/1978 | Grier et al. .................. 544/215 |
| 4,145,426 | 3/1979 | Grier et al. .................. 424/267 |

OTHER PUBLICATIONS

Albert and Clark, J.C.S., 1666–1673, (1964).
Japanese Patent Abstract, 51 64606, (197a).

*Primary Examiner*—Robert W. Ramsuer
*Attorney, Agent, or Firm*—Raymond M. Speer; Salvatore C. Mitri

[57] ABSTRACT

Antimicrobial compounds of the formula:

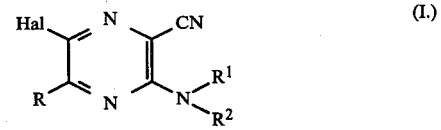

(I.)

wherein:
Hal is bromine or chlorine; and
R is halo; mono- or di-substituted mono- or diloweralkylamino wherein the loweralkyl substituents are hydroxy or loweralkanoyloxy; 4-morpholino; thiocyano; mercapto; straight or branched chain $C_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;
$R^1$ is hydrogen; or loweralkyl;
$R^2$ is $(CH_2)_nCOOR^3$, where $R^3$ is hydrogen, loweralkyl, or benzyl; and n is 1 to 3; and
$R^1$ and $R^2$ are taken together with an oxygen or nitrogen atom to form morpholino, piperazinyl, or piperazinyl which is N-loweralkyl substituted; are useful in various agricultural and industrial areas.

14 Claims, No Drawings

2-(SUBSTITUTED)AMINO-3-CYANO-5-HALO-6-(SUBSTITUTED)-PYRAZINE ANTIMICROBIAL COMPOUNDS, COMPOSITIONS AND USE

BACKGROUND OF THE INVENTION

1. Field of the Invention

The present invention is concerned with novel compounds which are 2-(substituted)amino-3-cyano-5-halo-6-(substituted)pyrazines.

The present invention is also concerned with antimicrobial compositions containing these novel compounds as active ingredients, as well as with a method of inhibiting the growth of bacteria and fungi by contacting said bacteria and fungi with the novel compounds of the present invention. These novel compounds have a number of important industrial and agricultural applications.

As used herein, the terms "antimicrobial", "bactericidal", and "fungicidal" describe the killing of, as well as the inhibition of or control of the growth of bacteria and fungi. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber, and machine industries. Important applications of the novel antimicrobial compounds of the present invention include: inhibiting the growth of bacteria in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as an additive to polyvinylchloride and other plastics to prevent growth thereon and degradation thereof by bacteria and fungi; as a component of antifouling paints to prevent adherence of fouling organisms; protecting paint films, especially exterior paints, from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing for example, and which are susceptible to degradation by microorganisms during storage and transport; and as a hard surface disinfectant to prevent growth of bacteria and fungi on walls, floors, etc. The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

Another important area where control of bacterial and fungal growth is vital is in clay and pigment slurries. These slurries are of various clays, e.g. kaolin, and pigments, e.g. calcium carbonate and titanium dioxide, and are manufactured usually at a location separate from the end use application, in for example, paper coating and paint manufacturing, and are then stored and held for later transport to the end use location. Because of the high quality standards for the paper and paint final products in which the slurry is used, it is essential that the clay or pigment slurry have a very low microorganism count or content so that it is usable in the paper coating or paint manufacturing.

The novel antimicrobial compounds of the present invention may also be utilized for agricultural and animal health applications, for example in preventing or minimizing the growth of harmful bacterial and/or fungi on plants, trees, fruit, seeds, or soil. At the same time there is obtained by their use a pronounced growth-stimulating action producing not only an abundant root system but also a luxuriant growth above ground, this being accompanied by a substantial increase in the yield of the crop per acre as compared not only with untreated plants and soils, but also with other, widely used foliar and soil fungicides. The novel antimicrobial compounds are especially useful in treating seed to prevent microorganism, particularly fungal attack. The novel antimicrobial compounds are also useful in protecting animal dip compositions against the buildup of microorganisms, and for this purpose may be combined with a veterinary animal dip parasiticide and an acceptable carrier.

The novel antimicrobial compounds of the present invention have been found especially useful in controlling the harmful effects of microorganisms in water or aqueous media. Systems which utilize circulating water or aqueous media become infected with microorganisms and experience substantial impairment of thier efficiency when deposits of the microorganisms build up in the system. The deposits, called slimes, coat the walls of tanks and other vessels, and any machinery or processing equipment which is employed, and create blockages in pipes and valves. The slimes also create discolorations and other imperfections in any products being produced, forcing costly shutdowns. Control of microorganisms in aqueous media is particularly important where there are dispersed particles or fines in the aqueous media, e.g., dispersed cellulosic fibers and dispersed fillers and pigments in papermaking, and dispersed pigments in paint manufacture.

2. Brief Description of the Prior Art

Cragoe and Jones, U.S. Pat. Nos. 3,274,192; 3,299,063; 3,341,540; and 3,487,082 all disclose various pyrazine compounds useful as diuretics. However, the novel pyrazines of the present invention are not suggested, nor is their use as antimicrobial agents.

Donald, U.S. Pat. No. 4,054,655 describes the use of aminodicyanopyrazines for controlling plant diseases caused by fungi. However, the novel pyrazines of the present invention are not suggested.

Grier et al., U.S. Pat. Nos. 4,145,426; 3,626,060; and 4,119,779 all describe various antibacterial and antifungal compounds for agricultural and industrial use. However, none of these compounds are pyrazines, and the novel pyrazines of the presnt invention are not suggested.

Kohn and Singer, U.S. Pat. Nos. 3,854,000 and 3,763,176 describe the use of certain thiadiazolin-4-ones as antimicrobial agents. However, the novel pyrazines of the present invention are not suggested.

Albert and Clark, J.C.S., 1666–1673 (1964), describe various pyrazines. However, no use for these pyrazines is suggested, and the novel pyrazines of the present invention are not suggested.

Kyowa published Japanese application No. 5164-606 describes 2,3-dicyanopyrazine compounds used as antimicrobial agents. However, there is no suggestion of the novel pyrazine compounds of the present invention.

DETAILED DESCRIPTION OF THE INVENTION AND PREFERRED EMBODIMENTS

In accordance with the present invention there is provided a novel 2-(substituted)amino-3-cyano-5-halo-6-(substituted)pyrazine antimicrobial compound of the formula:

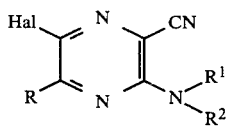  (I.)

wherein:
Hal is bromine or chlorine; and
R is halo; mono- or di-substituted mono- or diloweralkylamino wherein the loweralkyl substituents are hydroxy or loweralkanoyloxy; 4-morpholino; thiocyano; mercapto; straight or branched chain $C_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;
$R^1$ is hydrogen; or loweralkyl;
$R^2$ is $(CH_2)_n COOR^3$, where $R^3$ is hydrogen, loweralkyl, or benzyl; and n is 1 to 3; and
$R^1$ and $R^2$ are taken together with an oxygen or nitrogen atom to form morpholino, piperazinyl, or piperazinyl which is N-loweralkyl substituted.

The loweralkyl substituents recited above represent, except where otherwise indicated, any of the variables of straight, branched, and unsaturated chain hydrocarbon radicals of from one to four carbon atoms, such as methyl, ethyl, n-propyl, i-propyl, n-butyl, i-butyl, t-butyl; or vinyl, allyl, butenyl, and the like.

The halo substituent represents bromo or chloro.

The loweralkoxy substituent represents a loweralkyl group as described above attached through an oxygen bridge.

The loweralkanoyl substituent represents a loweralkyl group attached through a carbonyl bridge.

The aryl substituent represents phenyl, naphthyl, or biphenyl.

Preferred 2-(substituted)amino-3-cyano-5-halo-6-(substituted)pyrazine compounds of the present invention are the following:
methyl[(5,6-dichloro-3-cyanopyrazinyl)amino]acetate;
benzyl[(5,6-dichloro-3-cyanopyrazinyl)amino]acetate;
6-chloro-5-(methylthio)-3-(4-morpholino)pyrazinecarbonitrile;
6-chloro-5-(n-propylthio)-3-(4-morpholino)pyrazinecarbonitrile;
6-chloro-3,5-di-(4-morpholino)pyrazinecarbonitrile;
6-chloro-5-(dimethylamino)-3-(4-morpholino)pyrazinecarbonitrile;
5,6-dichloro-3-(4-morpholino)pyrazinecarbonitrile;
5,6-dichloro-3-(N-methylpiperazinyl)pyrazinecarbonitrile.

In accordance with the present invention there is further provided an antimicrobial composition comprising a carrier and an antimicrobially effective amount of a novel pyrazine of Formula I.

The novel pyrazine antimicrobial compound active ingredient of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the novel pyrazine antimicrobial compound is liquid, it may be employed neat or may be incorporated into various formulations, both solid and liquid, as an adsorbate on suitable inert carriers such as talc, clays, diatomaceous earth and the like.

Thus, it will be appreciated that the novel pyrazine antimicrobial compounds may be employed to form antimicrobial formulations containing one or more of the compounds as the essential active ingredient, which formulations may also contain a variety of carrier materials adaptable to industrial and agricultural applications including finely divided dry or liquid diluents, extenders, clays, diatomaceous earth, talc and the like, or water and various organic liquids such as loweralkanols, kerosene, benzene, toluene and other petroleum distillate fractions or mixtures thereof.

Antimicrobial compositions suitable for application to inanimate surfaces of growing plants or crops, which contain the novel pyrazine antimicrobial compounds of this invention, may be compounded in a variety of conventional formulations. However, such formulations must take account of the solubility characteristics of the particular novel pyrazine antimcirobial compounds utilized in the present invention. For example, the pyrazines are soluble in paraffinic oils such as xylene to an extent of less than 2%, whereas solubility of the order of 20 to 40% would be required to employ such oils as formulation media. On the other hand, such oils as do provide the required solubility for the pyrazines are not usefuL in preparing agricultural formulations because of cost, toxicity, etc.

The novel pyrazine antimicrobial compounds utilized in the present invention can be formulated as suspension concentrates or "flowable" formulations in either an oil or water base. Such formulations must include the proper amounts and types of suspending agents or emulsifiers, and preferably also stabilizers, spreading agents, an sticking agents. Well-known techniques and materials are employed in preparing these formulations. Suitable emulsifiers or suspending agents include both cationic and nonionic compounds such as sodium alkyl sulfates ("Dreft"), alkyl and alkyl-aryl sulfonates ("Nacconal N.M." and Dupont "MP-189"), alkyl-aryl polyester alcohols ("Spans"), and ethylene oxide addition products ("Tweens"). The nonionics are the preferred surfactants and include alkylphenol-ethylene-oxide condensation products such as isooctylphenol-polyethylene oxide condensates ("Triton X-100"), the various "spans" (sorbitan monopalmitate, stearate or oleate) and "Tweens" (e.g., sorbitan monolaurate-"Tween 20"). These materials can constitute from 0.05 to 10 percent of the active agents.

It is desirable to include a sticking agent or adhesive in the composition in the range of about ½ to 5 percent of the active material. These can be in the form of resins which are soluble or dispersible in water, and includes cellulose ethers, waxes, polyvinyl pyrrolidine, and powdered polyethylene. Sticking agents may also be included in small proportion (about ½ to 5 percent of the active substance), these including glycerine and nonvolatile polyethylene glycols.

For agricultural use these formulations may be diluted with water and applied to the foliage or soil. Adjuvants can be mixed with the active material before use or they may be sold as such in the dry condition admixed with the active material. The mixture then may be added to water just prior to use.

The emulsifying or suspending agents all, both singly and in admixture, serve the function of uniformly distributing the active ingredient in the aqueous or organic emulsions or suspensions, marketed as concentrates so that on mixing with water by the user there is produced a uniform mixture for application to the soil, seeds or plants.

The novel pyrazines utilized in the present invention may also be formulated as wettable powders.

For formulating wettable powders, various adjuvants and suspending agents can be employed such as are listed in Soap and Chemical Specialties, Volume 31, Number 7, p. 61 Ed. Seq.; No. 8 pp. 48–61; No. 9, pp. 52–57 and No. 10 pp. 38–67 (1955) and in Bulletin No. 607 of the Bureau of Entomology and Plant Quarantine, Department of Agriculture, Washington, D.C. The suspending agents include detergents of various kinds.

In the form of liquid concentrates or wettable powders as described above, the active component can comprise from 5 to 90 percent by weight of the composition, the remainder being the liquid carrier which can include any of the agents discussed above.

The novel pyrazines may also be formulated as dusts or granular formulations.

For use in the form of a dust or granular formulation the novel pyrazines may be blended with any suitable proportion of a variety or excipients including diluents, suspending and spreading agents and other adjuvants in pulverulent form (preferably below 50 micron particle size). Usually, the inert carrier will range in percentage composition from about 1 to 80 percent of the total composition and will include about one to five parts of a dispersing agent for 100 parts of active compound.

Suitable diluents include natural clays such as china clays, talc, bentonite, attapulgites and other similar inert material, and also pyrophyllites, diatomaceous earth, fuller's earth, chalk, rock phosphates, and also chemically modified minerals such as acid-washed bentonite, precipitated calcium phosphate and carbonate, colloidal silica, mica, pumice, vermiculite, wood flour, and grain flours. There can also be employed inert metal oxides and hydroxides such as titanium dioxide, aluminum oxide, and bauxite. Diluents such as clays, talc, bentonite and other mineral powders may be oil treated to increase their adhesivity; the oil being either a mineral hydrocarbon oil or a vegetable oil or an animal fatty oil.

The novel pyrazines utilized in the present invention may also be formulated as solutions in gamma-butyrolactone or N-methylpyrrolidinone. These solutions may be used as such or may additionally include additives of the types described in detail above. These solutions may also serve as the basis for other types of formulations as described in detail above.

The compositions can include various insecticides which are nonreactive with the novel pyrazine antimicrobial compound.

It will be understood also that the novel pyrazine antimicrobial compound active ingredients may be used in combination, where compatible, with other antimicrobial materials. For example, the novel pyrazine compounds can be combined with other fungicides and bactericides such as 2-(4'-thiazolyl)benzimidazole, sorbic acid, propionic acid, mycostatin, sodium diacetate, trichomycin, amphotericin, griseofulvin, undecylenic acid, esters of parahydroxybenzoic acid, chlorguinaldol, 5,7-dichloro-8-hydroxyquinoline, sodium-o-phenylphenate, o-phenylphenol, biphenyl chlorinated phenols, and sodium benzoate, in appropriate concentrations and in appropriate instances so as to combine the action of each to obtain particularly useful results. Such combinations might find particular application in the preparation of germicidal soaps, in the production of cosmetics and aqueous coatings and in combatting paper mill slime accumulations.

In accordance with the present invention there is still further provided a method of inhibiting the growth of at least one of: bacteria and fungi comprising contacting said bacteria and fungi with a bactericidally and fungicidally effective amount of a novel pyrazine antimicrobial compound of Formula I.

The antimicrobial methods of treatment of the present invention involve contacting the microorganisms involved with the novel pyrazine antimicrobial compound. This can be accomplished by simple addition of the compound. The article or system being treated will thus have incorporated therein or have applied thereto the desired dosage concentration of the compound.

As noted above, the instant invention is based upon the discovery that the novel pyrazine antimicrobial compounds described above are effective in controlling the growth of bacteria and fungi in a variety of industrial and agricultural applications. It has been found, for example, that the novel pyrazine compounds are effective antimicrobials for the destruction or control of soil fungi and bacteria and for the protection of seeds, bulbs and plants. The utility of the novel pyrazine antimicrobial compounds of this invention is shown not only by their activity against bacteria and fungi responsible for stunting growth, and even destruction of many types of crop-producing plants, but also against those causing degradation and deterioration of many types of industrial products including, for example, paper, leather, textiles, aqueous systems such as adhesives, resins, drilling fluids, pigment dispersions and latex paints and oleoresinous coatings whose films are particularly vulnerable to the destructive action of fungi. The large economic losses encountered in paper-making operations caused by the accumulation of bacterial and fungal slimes in various parts of the system can be eliminated to a significant extent by use of the novel pyrazine compounds described herein.

Thus, for pulp and paper mill systems, there is provided a method of inhibiting the growth of slime-forming bacteria and fungi, usually encountered in pulp and paper mill systems, comprising incorporating into the mass of fiber and water in such a pulp and paper mill system so as to contact said bacteria and fungi, at least a bactericidally and fungicidally effective amount of a novel pyrazine antimicrobial compound of Formula I.

There is further provided a method of inhibiting the growth of bacteria and fungi in aqueous slurries of clays or pigments comprising incorporating into said aqueous slurry so as to contact said bacteria and fungi, at least a bactericidally and fungicidally effective amount of a novel pyrazine antimicrobial compound of Formula I.

There is still further provided a method of inhibiting the growth of bacteria and fungi in latex paints and latex emulsions and adhesives comprising incorporating into said latex paints, emulsions, and adhesives so as to contact said bacteria and fungi, at least a bactericidally and fungicidally effective amount of a novel pryazine antimicrobial compound of Formula I.

There is yet further provided a method of inhibiting the growth of bacteria and fungi in metalworking fluids comprising incorporating into said fluids so as to contact said bacteria and fungi, at least a bactericidally and fungicidally effective amount of a novel pyrazine antimicrobial compound of Formula I.

There is yet further provided a method of protecting soil, seeds, plants and crops against destructive bacteria and fungi which comprises applying thereto at least a bactericidally and fungicidally effective amount of a novel pyrazine compound of Formula I.

The antimicrobial activity of the compounds described above has been confirmed using standard laboratory techniques. They have been found effective, for example, in inhibiting bacteria including *Aerobacter aerogenes, Pseudomonas aeruginosa, Escherichia coli, Staphylococcus aureus, Streptococcus pyogenes, Bordetella brontiseptica, Klebsiella pneumoniae,* and *Proteus mirabilis.* They have been found effective also against fungi including *Ustilago zeae, Alternaria solani, Botrytis allii, Helminthosporium cynodontis, Verticillium serrae, Fusarium oxysporum,* and *Pullularia pullulans.* Such bacteria and/or fungi commonly are found on cereal and grain products, in clay and pigment slurries, in oils, on fruits and vegetables and on cosmetics, leather, electrical insulation, textiles and numerous other materials capable of supporting their growth. Also, such bacteria and/or fungi may be found on plants, seeds, fur and wood and in soils.

As noted above, it has been found that growth of various harmful fungi and bacteria existing in soil is eliminated or limited by use of formulations containing the novel pyrazine antimicrobial compounds described herein. The term "soil" as used here is intended to include all media capable of supporting growth of plants and may include humus, sand, manure, compost, artificially created plant growth solutions and the like.

The novel pyrazine antimicrobial compounds described above have activity against bacteria and fungi when employed at appropriate levels of concentration and may be used to inhibit growth of these organisms. It will be obvious to those skilled in the art that the required effective concentration will vary with particular organisms and in particular applications. In general, however, effective fungicidal and bactericidal response is obtained when the novel pyrazine antimicrobial compound is employed in concentrations ranging between 10 and 1000 ppm (parts per million).

For latex paints, latex emulsions and adhesives, amounts of from 100 to 1000 ppm, preferably 200 to 500 ppm, of a novel pyrazine of Formula I are added during manufacture of the paint, emulsion, or adhesive in order to protect the system during in-can storage against bacteria and fungi.

For aqueous clay and pigment slurries, amounts of from 10 to 250 ppm, preferably 75 to 200 ppm of a novel pyrazine Formula I are added to said slurries in order to inhibit the growth of bacteria and fungi in said slurries; and for pulp and paper mills, amounts of from 50 to 250 ppm, preferably 100 to 200 ppm, of a novel pyrazine of Formula I, are added to the pulp suspension in a paper mill in order to inhibit the growth of slime-forming bacteria and fungi.

For metalworking fluids, i.e. cutting oils, amounts of from 100 to 1000 ppm, preferably 250 to 750 ppm, of a novel pyrazine of Formula I, are added in order to inhibit the growth of bacteria and fungi during the use cycle of an oil-water lubricant for metal surfaces.

Both in the powdered and in the liquid forms, the novel pyrazine compounds and compositions of this invention can be used as seed dressing to destroy seed-borne fungus spores and bacteria, both to increase the percentage germination and to protect the young plants and roots systems. Further, young plant roots can be dipped in such compounds and compositions to protect them against fungal attack.

The novel pyrazine compounds and compositions of the present invention can be used with advantage in sterilizing the soil on which are grown various vegetables, fruits and other agricultural products, such as beans, soy beans, sugar beets, carrots, cucumbers, cabbage, corn, peanuts, tomatoes, cotton, alfalfa, oats and clover, among others, and can also be applied to seeds ad plants to protect them against destructive microorganisms.

For such applications, the novel pyrazine compounds of Formula I may be employed in amounts of from 2 to 200 ppm, preferably 5 to 100 ppm.

For soil applications, generally, it is best to apply the composition to the top of the ground and then turn the soil over. Thus, 60 gallons of water can contain 5 pounds of the active substance to be applied per acre, thus yielding 5 ppm when the soil is turned over to depth of 3 inches. (At a 3 inch depth, 1 pound of antibacterial substance per acre is equivalent approximately to 1 ppm.) In case of cotton, for which the soil need be turned over for only a 2" depth, a correspondingly smaller amount of the active compound need be used. On the other hand, when the soil is plowed or turned over to a depth of 6", as for potatoes, a correspondingly larger amount is used.

The new compositions are effective also against the various fungi that infest fruit trees. Thus, apple trees can be sprayed, before fruit set, with an aqueous suspension, prepared by mixing, say, 100 gallon of water with an amount of the commercially prepared composition containing a novel pyrazine compound for Formula I such that 5 to 20 ppm are contained in the spray suspension. Other fruit trees like peach and cherry, can be treated in similar fashion.

For other applications of the type described above, amounts of from 0.005 to 0.05% by weight, based on weight of the substrate being treated, of a novel antimicrobial compound of the present invention is incorporated into, sprayed onto, used to dip, or otherwise applied to the substrate to be treated in order to prevent growth of bacteria and fungi.

Of course, the precise dosages of the novel pyrazine compounds which will be employed depends upon a number of factors. First, the dosage is indicated in parts per million (ppm), which refers to the concentration of the active ingredient in the environment being treated, for example, the concentration of a particular novel pyrazine in a clay slurry. This concentration is based on 100% active ingredient for convenience in evaluating and comparing test data. In actual practice, however, various percentages of active ingredient may actually be used, with the balance of the composition being added comprising conventional excipients such as dispersants, stabilizers, preservatives, co-solvents, diluents, and the like.

The novel pyrazine antimicrobial compounds of Formula I may be prepared in accordance with the following illustrative reaction schemes:

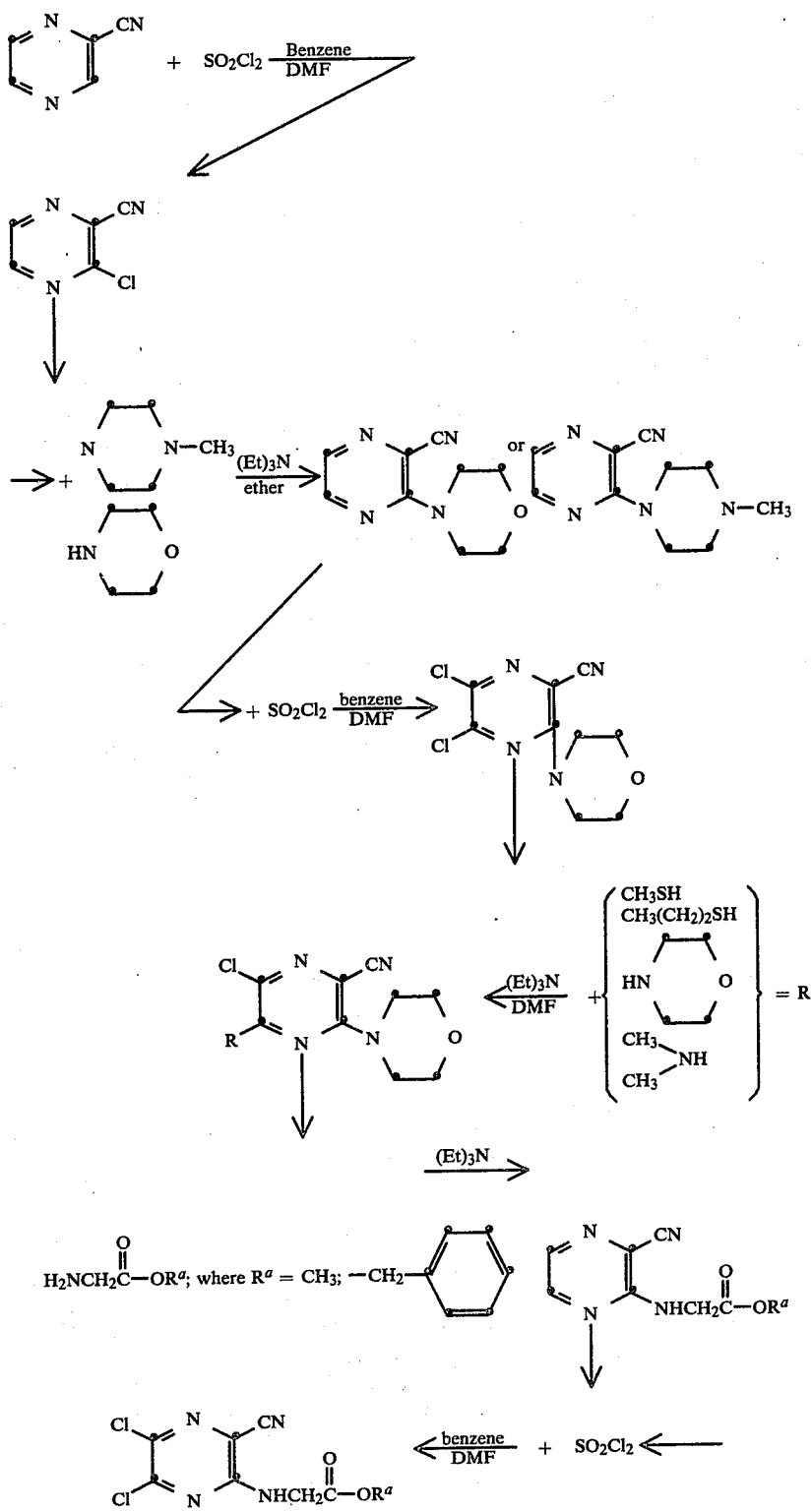

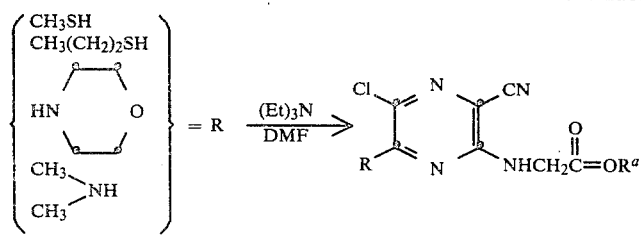

Where R is loweralkanoyloxy-substituted loweralkamino, the novel pyrazine of Formula I may simply be prepared from the corresponding hydroxy-substituted loweralkylamino pyrazine by treating it with the appropriate lower alkanoic acid anhydride, e.g., acetic anhydride. Similarly, where R is loweralkanoylamino-substituted loweralkylthio, the novel pyrazine of Formula I may be prepared from the corresponding amino-substituted loweralkylthio pyrazine by treating it with the appropriate loweralkanoic acid anhydride, e.g., acetic anhydride.

Where R is thiocyano, the novel pyrazine of Formula I may be prepared by treating the starting material with ammonium thiocyanate.

The following examples will serve to further illustrate the present invention, without at the same time, however, constituting any limitation thereof.

EXAMPLE 1

Methyl[(5,6-dichloro-3-cyanopyrazinyl)amino]acetate

A. Cyanopyrazine

In 100 ml of phosphoryl chloride at reflux temperature there was stirred pyrazineamide (20 g; 0.162 M) for 1 hour. Excess phosphoryl chloride was then removed and water aspirated. Ice was added to the residue, followed by sodium carbonate until basic, the extraction with 150 ml of ether five times. The combined extracts were dried over sodium sulfate, and the solvent then removed in vacuo to give title compound (12.9 g).

B. Chlorocyanopyrazine

In 90 ml of benzene and 9.2 ml of dimethylformamide there was stirred at room temperature cyanopyrazine (12.7 g; 0.12 M) prepared in Step A above, after which there was added over 10 minutes sulfonyl chloride (64.79 g; 0.48 M). The reaction mixture was stirred for 30 minutes in an ice bath, then allowed to warm up to room temperature gradually, after which it was stirred for 5 hours. The benzene layer was decanted, and the reddish oil residue was extracted three times with ether, after which the combined benzene and ether layers were quenched with ice water and cooled in an ice bath. The combined layers were then neutralized with solid sodium bicarbonate, then separated, and the aqueous layer was extracted with ether. The combined organic layers were washed once with a small amount of water, dried with sodium sulfate, filtered, and the solvent evaporated to give the title compound (11 g).

C. Methyl [(3-cyanopyrazinyl)amino]acetate

In 8 ml of ether there was dissolved chlorocyanopyrazine (0.42 g; 0.003 M) prepared in Step B above, after which there was added glycine methyl ester hydrochloride (378 mg; 0.003 M), followed by triethylamine (607 mg, 0.84 ml; 0.006 M). The reaction mixture was stirred at room temperature overnight. The resulting precipitate was filtered, washed twice with ether, and the filtrate concentrated under vacuum, then passed through a silica gel column and eluted with dichloromethane to give the title compound (130 mg).

D. Methyl [(5,6-dichloro-3-cyanopyrazinyl)amino]-acetate

In 10.04 ml of dimethylformamide (sieves) and 0.3 ml of benzene (sieves) there was dissolved methyl [(3-cyanopyrazinyl)amino]acetate (86 mg; 0.0005 M) prepared in Step C above, after which there was added sulfonyl chloride (0.270 mg; 0.16 ml; 0.002 M). The reaction mixture was stirred at room temperature overnight, then cooled in an ice bath, after which there was added ether and pieces of ice. The reaction mixture was neutralized with sodium bicarbonate, the layers were separated, and the organic layer was washed with water. The aqueous layer was extracted twice with ether, dried, and the solvent evaporated, then passed through a silica gel column and eluted with dichloromethane to give the title compound (68 mg). Elemental Analysis for $C_8H_6N_4O_2Cl_2$.

|         | % C   | % H  | % N   | % O   | % Cl  |
|---------|-------|------|-------|-------|-------|
| Calc'd: | 36.80 | 2.31 | 21.46 | 12.25 | 27.16 |
| Found:  | 36.75 | 2.30 | 20.92 | —     | —     |

EXAMPLE 2

Benzyl [(5,6-dichloro-3-cyanopyrazinyl)amino]acetate

A. Benzyl [(3-cyanopyrazinyl)amino]acetate

Following the procedures described in Example 1, Step C above, but substituting glycine benzyl ester toluene sulfonate (1.01 g; 0.003 M) for the glycine methyl ester hydrochloride, there was prepared the title compound (72 mg).

B. Benzyl [(5,6-dichloro-3-cyanopyrazinyl)amino]-acetate

In 0.02 ml of dimethylformamide (sieves) and 0.15 ml of benzene (sieves) was dissolved benzyl [(3-cyanopyrazinyl)amino]acetate (72 mg; 0.00025 M) prepared in Step A above, after which there was added sulfonyl chloride (135 mg; 0.08 ml; 0.001 M). The product was worked up in the manner described in Example 1, Step D above, to give 59 mg. Elemental Analysis for $C_{14}H_{10}N_4O_2Cl_2$:

|        | % C   | % H  | % N   | % O  | % Cl  |
|--------|-------|------|-------|------|-------|
| Calc'd | 49.87 | 2.99 | 16.62 | 9.49 | 21.03 |
| Found  | 49.02 | 3.05 | 16.16 | —    | —     |

EXAMPLE 3

6-Chloro-5-(methylthio)-3-(4-morpholino)pyrazinecarbonitrile

A. 3-(4-Morpholino)pyrazinecarbonitrile

Following the procedures described in Example 1, Step C above, but substituting morpholine (0.28 g; 0.28 ml; 0.0033 M) for the glycine methyl ester hydrochloride, there was prepared the title compound (520 mg).

B. 5,6-Dichloro-3-(4-morpholino)pyrazinecarbonitrile

Following the procedures described above in Example 1, Step D, there was obtained the title compound as a yellowish oil (600 mg). Elemental Analysis for $C_9H_8N_4OCl_2$:

|  | % C | % H | % N | % O | % Cl |
|---|---|---|---|---|---|
| Calc'd | 41.72 | 3.11 | 21.62 | 6.17 | 27.37 |
| Found | 41.56 | 3.13 | 21.41 | — | 26.56 |

C. 6-Chloro-5-(methylthio)-3-(4-morpholino)pyrazinecarbonitrile

In 5 ml of dry dimethylformamide there was stirred 5,6-dichloro-3-(4-morpholino)pyrazine-carbonitrile (0.75 g; 2.896 Moles) prepared in Step B above, after which the resulting solution was chilled and there was then passed therethrough methane thiol gas for 10 minutes. Triethylamine (293 mg; 2.896 Moles) was then added and the reaction mixture was stirred cold, then allowed to come to room temperature, for a total time of 4 hours. The reaction mixtre was then blown down under nitrogen and a solid yellow precipitate resulted. After attempted partition between water and ether, dichloromethane was added, and the aqueous portion was extracted twice with dichloromethane. The organic extracts were dried over sodium sulfate, filtered, blown down under nitrogen overnight to give 780 mg of crude product, which was then recrystallized from 12 ml of isopropanol and filtered to give the title compound (680 mg; 87%); m.p. 138°–139° C. Elemental Analysis for $C_{10}H_{11}N_4OClS$:

|  | % C | % H | % N | % Cl | % S |
|---|---|---|---|---|---|
| Calc'd | 44.36 | 4.10 | 20.69 | 13.10 | 11.84 |
| Found | 44.48 | 3.87 | 20.71 | 12.82 | 11.78 |

EXAMPLES 4–6

Following the procedures described above for Example 3, but substituting for the methane thiol employed in Step C, the appropriate thiol or amine reactant, there was obtained the following pyrazinecarbonitriles of Formula I:

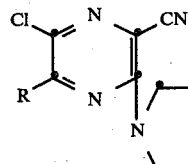

| Example No. | Amine or Thiol | | Elemental Analysis Calculated/Found | | | | |
|---|---|---|---|---|---|---|---|
|  |  |  | % C | % H | % N | % Cl | % S |
| 4 | $CH_2(CH_2)_2SH$ | $CH_3(CH_2)_2S-$ | 48.24 | 5.06 | 18.75 | 11.87 | 10.73 |
|  |  |  | 48.18 | 5.01 | 18.93 | 12.17 | 10.65 |
| 5 | HN⟨O⟩ | ⟨O⟩N— | 50.41 | 5.21 | 22.61 | 11.45 | — |
|  |  |  | 50.51 | 5.29 | 22.41 | 11.56 | — |
| 6 | $CH_3\!\!>\!\!NH$ $CH_3$ | $CH_3\!\!>\!\!N-$ $CH_3$ | 49.53 | 5.27 | 26.16 | 13.24 | — |
|  |  |  | 49.32 | 5.22 | 26.00 | 13.11 | — |

EXAMPLE 7

5,6-Dichloro-3-(N-methylpiperazinyl)pyrazinecarbonitrile

A. 3-(N-methylpiperazinyl)pyrazinecarbonitrile

Following the procedures described in Example 1, Step C above, but substituting N-methylpiperazine (0.33 g; 0.0033 Mole) for the glycine methyl ester hydrochloride, there was prepared the title compound (600 mg).

B. 5,6-Dichloro-3-(N-methylpiperazinyl)pyrazinecarbonitrile

Following the procedures described above in Example 1, Step D, there was obtained the title compound as a crystalline product (250 mg).

What is claimed is:

1. A compound of the formula:

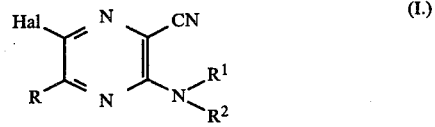

wherein:

Hal is bromine or chlorine; and

R is halo; mono- or di-substituted mono- or diloweralkylamino wherein the loweralkyl substituents are hydroxy or loweralkanoyloxy; 4-morpholino; thiocyano; mercapto; straight or branched chain $C_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

$R^1$ is hydrogen; or loweralkyl;

$R^2$ is $(CH_2)_n COOR^3$, where $R^3$ is hydrogen, loweralkyl, or benzyl; and n is 1 to 3; and $R^1$ and $R^2$ are taken together with an oxygen or nitrogen atom to form morpholino, piperazinyl, or piperazinyl which is N-loweralkyl substituted.

2. A compound according to claim 1 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)-pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

3. An antimicrobial composition comprising a carrier and an antimicrobially effective amount of a compound of the formula:

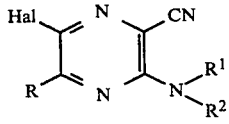   (I.)

wherein:

Hal is bromine or chlorine; and

R is halo; mono- or di-substituted mono- or diloweralkylamino wherein the loweralkyl substituents are hydroxy or loweralkanoyloxy; 4-morpholino; thiocyano; mercapto; straight or branched chain $C_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

$R^1$ is hydrogen; or loweralkyl;

$R^2$ is $(CH_2)_n COOR^3$, where $R^3$ is hydrogen, loweralkyl, or benzyl; and n is 1 to 3; and $R^1$ and $R^2$ are taken together with an oxygen or nitrogen atom to form morpholino, piperazinyl, or piperazinyl which is N-loweralkyl substituted.

4. A composition according to claim 3 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)-pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

5. A method of inhibiting the growth of bacteria and fungi comprising contacting said bacteria and fungi with a bactericidally and fungicidally effective amount of a compound of the formula:

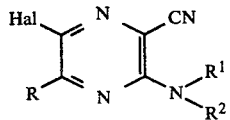   (I.)

wherein:

Hal is bromine or chlorine; and

R is halo; mono- or di-substituted mono- or diloweralkylamino wherein the loweralkyl substituents are hydroxy or loweralkanoyloxy; 4-morpholino; thiocyano; mercapto; straight or branched chain $C_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

$R^1$ is hydrogen; or loweralkyl;

$R^2$ is $(CH_2)_n COOR^3$, where $R^3$ is hydrogen, loweralkyl, or benzyl; and n is 1 to 3; and $R^1$ and $R^2$ are taken together with an oxygen or nitrogen atom to form morpholino, piperazinyl, or piperazinyl which is N-loweralkyl substituted.

6. A method according to claim 5 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)-pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

7. A method of inhibiting the growth of bacteria and fungi in aqueous slurries of clays or pigments comprising incorporating into said aqueous slurry so as to contact said bacteria and fungi, at least a bactericidally and fungicidally effective amount of a compound of the formula:

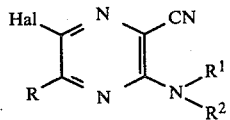   (I.)

wherein:

Hal is bromine or chlorine; and

R is halo; mono- or di-substituted mono- or diloweralkylamino wherein the loweralkyl substituents are hydroxy or loweralkanoyloxy; 4-morpholino; thiocyano; mercapto; straight or branched chain C$_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

R$^1$ is hydrogen; or loweralkyl;

R$^2$ is (CH$_2$)$_n$COOR$^3$, where R$^3$ is hydrogen, loweralkyl, or benzyl; and n is 1 to 3; and R$^1$ and R$^2$ are taken together with an oxygen or nitrogen atom to form morpholino, piperazinyl, or piperazinyl which is N-loweralkyl substituted.

8. A method according to claim 7 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)-pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

9. A method of inhibiting the growth of bacteria and fungi in latex paints and latex emulsions and adhesives comprising incorporating into said latex paints, emulsions, and adhesives so as to contact said bacteria and fungi, at least a bactericidally and fungicidally effective amount of a compound of the formula:

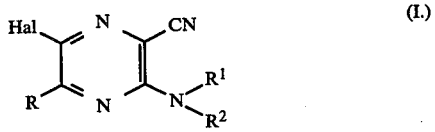

wherein:
Hal is bromine or chlorine; and
R is halo; mono- or di-substituted mono- or diloweralkylamino wherein the loweralkyl substituents are hydroxy or loweralkanoyloxy; 4-morpholino; thiocyano; mercapto; straight or branched chain C$_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

R$^1$ is hydrogen; or loweralkyl;

R$^2$ is (CH$_2$)$_n$COOR$^3$, where R$^3$ is hydrogen, loweralkyl, or benzyl; and n is 1 to 3; and R$^1$ and R$^2$ are taken together with an oxygen or nitrogen atom to form morpholino, piperazinyl, or piperazinyl which is N-loweralkyl substituted.

10. A method according to claim 9 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)-pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

11. A method of inhibiting the growth of bacteria and fungi in metalworking fluids comprising incorporating into said fluids so as to contact said bacteria and fungi, at least a bactericidally and fungicidally effective amount of a compound of the formula:

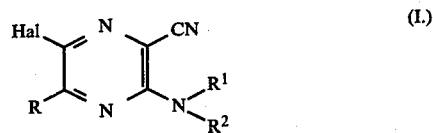

wherein:
Hal is bromine or chlorine; and
R is halo; mono- or di-substituted mono- or diloweralkylamino wherein the loweralkyl substituents are hydroxy or loweralkanoyloxy; 4-morpholino; thiocyano; mercapto; straight or branched chain C$_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

R$^1$ is hydrogen; or loweralkyl;

R$^2$ is (CH$_2$)$_n$COOR$^3$, where R$^3$ is hydrogen, loweralkyl, or benzyl; and n is 1 to 3; and R$^1$ and R$^2$ are taken together with an oxygen or nitrogen atom to form morpholino, piperazinyl, or piperazinyl which is N-loweralkyl substituted.

12. A method according to claim 11 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

13. A method for protecting soil, seeds, plants and crops against destructive bacteria and fungi which comprises applying thereto a bactericidally and fungicidally effective amount of a compound of the formula:

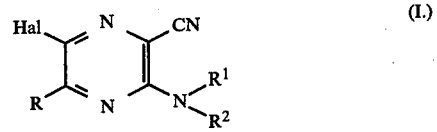

wherein:
Hal is bromine or chlorine; and
R is halo; mono- or di-substituted mono- or diloweralkylamino wherein the loweralkyl substituents are hydroxy or loweralkanoyloxy; 4-morpholino; thiocyano; mercapto; straight or branched chain $C_{1-8}$alkylthio; mono- or di-substituted loweralkylthio wherein the substituents are hydroxy, amino, loweralkanoylamino, or loweralkoxycarbonyl; arylthio; loweralkylsulfoxy; or loweralkylsulfonyl;

$R^1$ is hydrogen; or loweralkyl;

$R^2$ is $(CH_2)_n COOR^3$, where $R^3$ is hydrogen, loweralkyl, or benzyl; and n is 1 to 3; and $R^1$ and $R^2$ are taken together with an oxygen or nitrogen atom to form morpholino, piperazinyl, or piperazinyl which is N-loweralkyl substituted.

14. A method according to claim 13 wherein the compound is a member selected from the group consisting essentially of:

methyl [(5,6-dichloro-3-cyanopyrazinyl)amino]acetate;
benzyl [(5,6-dichloro-3-cyanopyrazinyl)amino]acetate;
6-chloro-5-(methylthio)-3-(4-morpholino)-pyrazinecarbonitrile;
6-chloro-5-(n-propylthio)-3-(4-morpholino)-pyrazinecarbonitrile;
6-chloro-3,5-di-(4-morpholino)pyrazinecarbonitrile;
6-chloro-5-(dimethylamino)-3-(4-morpholino)-pyrazinecarbonitrile;
5,6-dichloro-3-(4-morpholino)pyrazinecarbonitrile;
5,6-dichloro-3-(N-methylpiperazinyl)pyrazinecarbonitrile.

* * * * *